United States Patent
Westmarland et al.

(10) Patent No.: US 8,747,636 B2
(45) Date of Patent: Jun. 10, 2014

(54) LOW WATER VAPOUR TRANSFER COATING OF THERMOPLASTIC MOULDED OXYGEN GAS SENSORS

(75) Inventors: Paul Westmarland, Esher (GB); Dan Hawkinson, Elburn, IL (US); Tony Downer, Portsmouth (GB)

(73) Assignee: Life Safety Distribution AG, Uster (CH)

( * ) Notice: Subject to any disclaimer, the term of this patent is extended or adjusted under 35 U.S.C. 154(b) by 53 days.

(21) Appl. No.: 13/412,261

(22) Filed: Mar. 5, 2012

(65) Prior Publication Data

US 2012/0228140 A1    Sep. 13, 2012

Related U.S. Application Data

(60) Provisional application No. 61/451,793, filed on Mar. 11, 2011.

(51) Int. Cl.
  *G01N 27/30* (2006.01)
(52) U.S. Cl.
  USPC ......... 204/432; 73/23.31; 73/23.32; 204/424; 204/431
(58) Field of Classification Search
  USPC ......... 204/421–431, 400, 412, 415; 73/23.31, 73/23.32
  See application file for complete search history.

(56) References Cited

U.S. PATENT DOCUMENTS

| | | | | |
|---|---|---|---|---|
| 5,281,324 A * | 1/1994 | Kiesele et al. | ............. | 204/415 |
| 6,129,825 A * | 10/2000 | Mallory et al. | ............. | 204/415 |
| 7,361,307 B2 * | 4/2008 | Shartle et al. | ............. | 422/82.01 |
| 2002/0134677 A1 * | 9/2002 | Peng | ............. | 204/402 |
| 2007/0148390 A1 * | 6/2007 | Kumar | ............. | 428/36.91 |
| 2010/0170795 A1 * | 7/2010 | Cowburn et al. | ............. | 204/406 |
| 2010/0297687 A1 * | 11/2010 | Mutharasan et al. | ............. | 435/29 |

FOREIGN PATENT DOCUMENTS

WO   WO 2006/121321 A1   11/2006
WO   WO 2008/082362 A1   7/2008

OTHER PUBLICATIONS

Charlson et al. (Mat. Res. Soc. Symp. Proc. vol. 154, 1989).*
European Search Report for corresponding EP application 12158460.1, mailing date Mar. 12, 2014.

* cited by examiner

*Primary Examiner* — Jennifer Dieterle
(74) *Attorney, Agent, or Firm* — Husch Blackwell LLP

(57) ABSTRACT

A gas sensor is disclosed. The gas sensor includes a gas sensing electrode and a counter electrode disposed within a housing, and respective conductors that connects the gas sensing electrode and the counter electrode to a sensing circuit. The housing includes walls defining a cavity containing electrolyte in fluid communication with the gas sensing electrode and counter electrode and wherein the walls further comprise one or more coatings or second layers superimposed on the walls. The one or more coatings or second layers have a lower water vapor transport rate than that of the walls, such that, in use, water vapor transport between the electrolyte and atmosphere through the walls of the housing is reduced.

16 Claims, 4 Drawing Sheets

$V_{OUT} = R_{GAIN} I_S$

LOW WATER VAPOUR TRANSFER COATING OF THERMOPLASTIC MOULDED OXYGEN GAS SENSORS

CROSS-REFERENCE TO RELATED APPLICATION

This application claims the benefit of the filing date of U.S. Provisional Application Ser. No. 61/451,793 filed Mar. 11, 2011 entitled, "Low Water Vapour Transfer Coating of Thermoplastic Moulded Oxygen Gas Sensors." The '793 application is hereby incorporated herein by reference.

FIELD

The field relates to electrochemical gas sensors for the detection of a target gas in an atmosphere and, more particularly, to oxygen sensors.

BACKGROUND

Electrochemical oxygen sensors traditionally comprise a gas diffusion working electrode, often based on a graphite/platinum catalyst dispersed on PTFE tape. Oxygen is reduced at this cathode while a balancing oxidation reaction takes place at a consumable anode (e.g., made of lead (Pb)). The electrodes are held within an outer housing which contains a liquid electrolyte capable of supporting the relevant reactions, such as aqueous potassium acetate. The gas under test typically enters the housing through a controlled diffusion access port which regulates the ingress of oxygen into the cell. As the oxygen is reacted at the cathode, the electrical output of the sensor may be directly related to the ambient oxygen concentration. Such principles are well known and have been described.

Electrochemical gas sensors have a finite lifetime which depends on a number of factors. For oxygen sensors, the primary factor is the consumption of electrode material (e.g. a consumable lead counter electrode). Most types of sensors can also suffer from a gradual loss of activity of one or both electrodes, caused by the water drying out of the electrolyte. Clearly it is desirable for the sensor's working lifetime to be as long as possible but moreover it is important that any particular sensor type will consistently continue to work for at least the indicated lifetime. Early failures lead to the need for more frequent sensor replacement, as well as increased checking and monitoring of sensor performance and, ultimately, a loss in confidence in the sensor. Accordingly, there is a need to produce sensors that are more stable under many different operating environments.

BRIEF DESCRIPTION OF THE DRAWINGS

Examples of electrochemical gas sensors and method of manufacture will now be described and contrasted with conventional sensors, with reference to the accompanying drawings, in which.

DETAILED DESCRIPTION OF AN ILLUSTRATED EMBODIMENT

Figure 1:
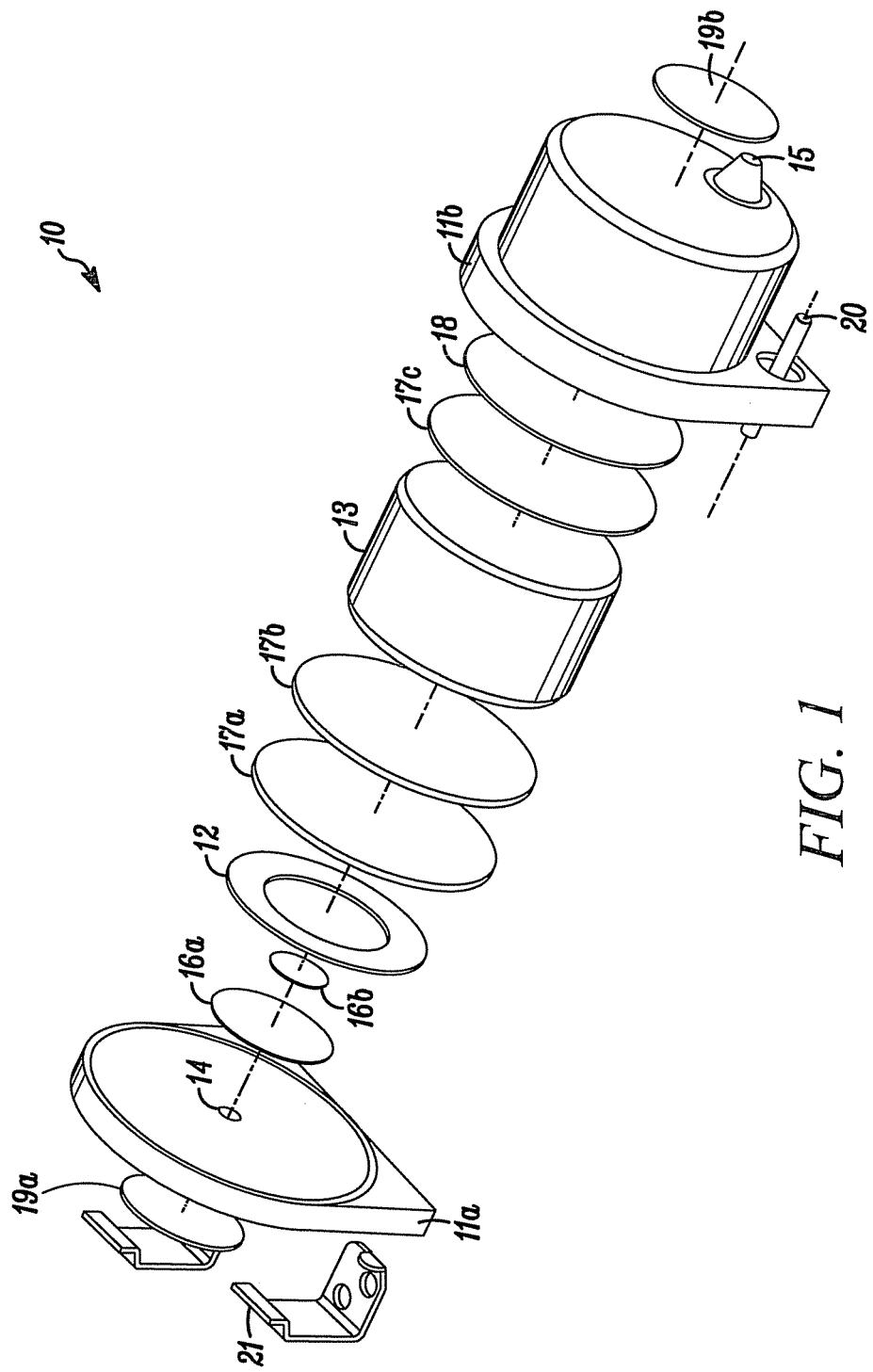
FIG. 1 is an exploded view of a electrochemical gas sensor shown generally in accordance with an illustrated embodiment.

FIG. 1 is an exploded view of an electrochemical gas sensor 10 shown generally, in accordance with one embodiment. The electrochemical gas sensor 10 may be used for the detection of a target gas in any of a number of different atmospheres. The sensor 10 includes a gas sensing electrode and a counter electrode disposed within a housing, and means, such as a conductor, for connecting the gas sensing electrode and the counter electrode to a sensing circuit, the housing is provided with an aperture for gas ingress and includes walls defining a cavity containing electrolyte in fluid communication with the gas sensing electrode and counter electrode, wherein the walls define the cavity. The walls define a first layer integral to the housing. To this first, integral layer, one or more coatings or second layers having a lower water vapor transport rate than that of the first layer is superimposed on the walls, such that, in use, water vapor transport from the electrolyte to the atmosphere through the walls of the housing is reduced.

By providing the housing walls with a layer or coating of a material with a relatively low water transport rate, it becomes possible to reduce the dehydration of the electrolyte through the walls without compromising the sensor design. It should also be noted that the layer or coating also operates to reduce absorption of water by the sensor. This can be important in very high humidity environments to eliminate the possibility of a sensor taking on water and bursting in extreme circumstances.

In particular, the body of the housing can be made of the necessary plastics material (such as ABS) for compatibility with manufacturing requirements, with the second layer or coating acting to reduce water vapor transport. As such, depletion of the electrolyte can be substantially reduced (relative to conventional sensors) while retaining a small sensor footprint and sufficient internal capacity. The lifetime of the sensor is prolonged, and in addition it becomes possible to use the sensor in more extreme environments (i.e. hotter and/or drier) than previously possible.

In order to achieve a reduction in electrolyte depletion, it is not necessary for the second layer to cover the entirety of the cavity walls, although this may be desirable in some cases. In many embodiments, however, it is preferred that the portion of the walls having the first and second layers comprises at least 50% of the walls defining the cavity, preferably at least 75%, still preferably at least 90%. The more of the cavity walls is coated with the second layer, the greater the reduction in water vapor transfer through the housing.

One reason that it may be desirable to leave certain parts of the cavity walls uncoated is where these parts are to undergo particular manufacturing processes, such as joining, cutting or otherwise, which such processes are tuned to perform best when applied to the material making up the main body of the housing (i.e. the material of the first layer). Therefore, preferably, the portion of the walls having the coating omits predetermined processing regions of the walls. Some or all of the remaining regions of the walls can include the coating. In particularly preferred embodiments, the processing regions comprises regions of the housing which, in use, form joints with one or more other components, preferably heat welded joints or ultrasonic welded joints. In other preferred embodiments, the processing regions may additionally or alternatively comprise regions of the housing which, in use, are laser-drilled.

The coating could be provided on either surface of the cavity wall, or even inside the cavity wall itself. In certain preferred embodiments, the coating of the wall is inboard of the first layer. This has the advantage that the coating is protected from external influences and, in particular, potential damage during handling. This is especially the case where the coating is very thin. However, in other cases it is preferable that the coating of the wall is outboard of the first layer. This may be advantageous if the coating is less thin, to avoid any reduction in anode capacity. Depending on the material and processing technique used to form the second layer, it may also be easier to apply the layer to the outside of the cavity walls rather than the interior.

So as to avoid any significant increase in the sensor dimensions, it is preferable that the coating is much thinner than the integral layer of the wall in the portion of the walls having the first and second layers. It should be noted that the thickness of the cavity walls may vary around the periphery of the cavity: for example, the side walls are typically thinner than the walls formed by a cap closing the top of the cavity. The second layer is preferably thinner than the first layer of the walls at any position, but this need not be the case.

In particularly preferred embodiments, the added layers of the wall have a thickness of less than 10 μm, although greater or lesser layers could be used. The thickness of the coating may vary across the wall as desired.

It has been found preferable that the integral layer of the wall in the portion of the walls having the first and second layers has a thickness of around 0.85 mm. This thickness will however depend largely on the type and design of the sensor. As noted above, the thickness of the integral layer may vary.

Advantageously, the water vapor transport rate of the coating is much lower than that the rate of the integral layer. The lower the water vapor transport rate, the thinner the coating need be in order to be effective.

Preferably, the housing and integral first layer of the walls comprises acrylonitrile butadiene styrene (ABS) or a polyphenylene oxide (PPO)/polystyrene (PS) blend. These materials have been found to have the desired properties for manufacture of the sensor, and in particular are well adapted for ultrasonic welding and laser drilling.

Advantageously, the added layer of the walls may be a polymer such as a parylene conformal "C" coating. In this case, the parylene "C" coating may be para-xylyene with a Cl atom substituted into its structure. The "C" variant of para-xylylene may be applied using a chemical vapor deposition (CVD) process, not requiring "line-of-sight" for the coating at a pressure of 0.1 torr. These materials have very low permeability to moisture and corrosive gases. This may be particularly important in order to insure that the coating is effectively inert towards the chemistry employed within the cell.

In certain preferred embodiments, at least the counter electrode is contained within the cavity such that in use it is at least partly immersed in electrolyte. This is generally the case, for example, in sensors having consumable electrodes, such as the aforementioned oxygen sensor. In other preferred embodiments, the housing contains one or more separators adapted to hold electrolyte therein and to supply electrolyte to the gas sensing electrode and the counter electrode, and the cavity comprises a reservoir containing electrolyte. In use, the sensor further comprises a wick for conveying electrolyte from the reservoir to the separator. This is often the case, for example, in toxic gas sensors.

Preferably, the gas sensing electrode comprises a catalyst dispersed on a backing tape, wherein the catalyst preferably comprises graphite and/or platinum, and the backing tape preferably comprises PTFE.

Advantageously, the counter electrode comprises a consumable electrode, the consumable electrode preferably comprising lead (Pb), zinc (Zn), copper (Cu) or iron (Fe). In alternative embodiments, the counter electrode could comprise a catalyst dispersed on a backing tape, akin to the above-described gas sensing electrode.

The sensor may operate with only two electrodes, the counter electrode also acting as a reference electrode, but in other preferred embodiments, the sensor further comprises a reference electrode, in which case the sensor can operate on the three electrode principle.

Preferably, the aperture for gas ingress comprises a diffusion limiting barrier, such as a capillary or a membrane.

The present description also provides a method of manufacturing an electrochemical gas sensor for the detection of a target gas in an atmosphere, the method comprising: forming a cavity portion of a housing, comprising integral walls defining a cavity; applying a coating to cover at least a portion of the walls defining the cavity, the layer having a lower water vapor transport rate than that of the integral walls; providing a gas sensing electrode and a counter electrode within the housing, and means for connecting the gas sensing electrode and the counter electrode to a sensing circuit, at least partially filling the cavity with electrolyte; and closing the cavity by providing a lid portion of the housing, comprising an aperture for gas ingress, and joining the lid portion to the cavity portion of the housing; whereby, in use, water vapor transport from the electrolyte to the atmosphere through the walls of the housing is reduced.

As described above, by applying a layer of material having a lower water vapor transport rate, dehydration of the electrolyte is reduced, while not compromising the mechanical performance of the housing.

Advantageously, the cavity portion (e.g. body) or integral layer of the housing is formed by a first molding step, preferably injection molding. In a particularly preferred embodiment, the coating (having a lower water vapor transport rate) is applied by CVD.

As discussed above, electrochemical gas sensors can suffer failure due to drying out of the electrolyte due to water vapor transfer through the housing walls. For small sensors, water vapor loss through apertures such as the capillary or vent is relatively insignificant.

It has been found that failure occurs for both vented and non-vented sensors when the original electrolyte volume has depleted by about 50%. The failure mechanism for vented sensors is usually a high signal output (due to oxygen breaking through from the vent) whereas the failure mechanism for non-vented sensors is typically extended response time and/or loss of output.

One way to reduce the loss of electrolyte through the walls of a sensor is to increase the wall thickness. Modeling of the electrolyte loss using water vapor transfer rates, and details of the mechanical design (thickness and surface area of walls in the sensor), with adjustments for temperature, humidity and expected variation in transfer rate of potassium acetate electrolyte compared to water can be used to estimate water loss. For example, a conventional sensor with a housing made of ABS, has a water vapor transfer rate of around 5.88 g mm/m$^2$/day at 37 degrees C. and 90% RH. Modeling shows the number of days until the electrolyte is depleted by 50%, as it varies with wall thickness, and assuming that the increase in wall thickness does not affect the internal dimensions of the sensor. It will be seen that, to achieve a 2-year lifetime at 22 C and 0% RH, an ABS wall thickness of around 2.25 mm is required.

However, existing conventional sensors have a wall thickness of around 0.85 mm, so the wall dimensions would need to be more than doubled in order to achieve the desired effect.

This simple model assumes that the internal volume of the sensor (and therefore the electrolyte volume and available space for the anode) is unchanged, so any additional wall thickness involves making the external size of the sensor larger. Increasing the overall size of the sensor (e.g. by around 2.8 mm in diameter to achieve a 2-year life), would have major implications for the instrument and is not desirable.

As an alternative, the internal geometry of the sensor could be reduced to allow for the additional wall thickness. This option will clearly impact on the available volume for the consumable anode and electrolyte in the sensor.

Figure 2A:
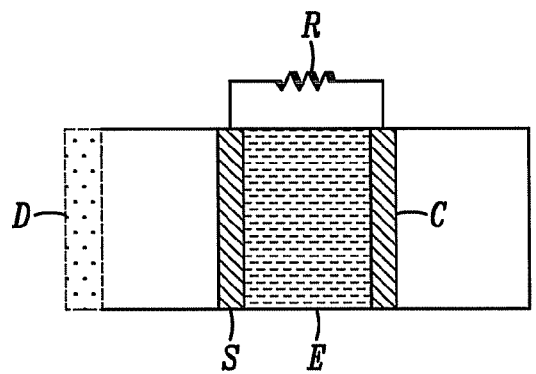
FIGS. 2a-c are circuits that may be used with the sensor of FIG. 1.
Figure 2B:
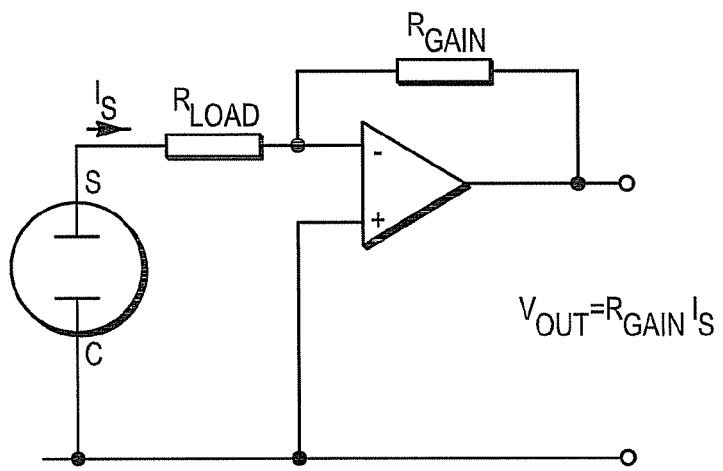
Figure 2C:
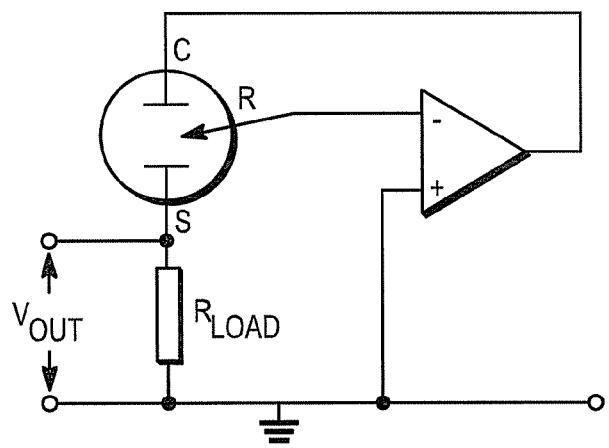
Figure 3:
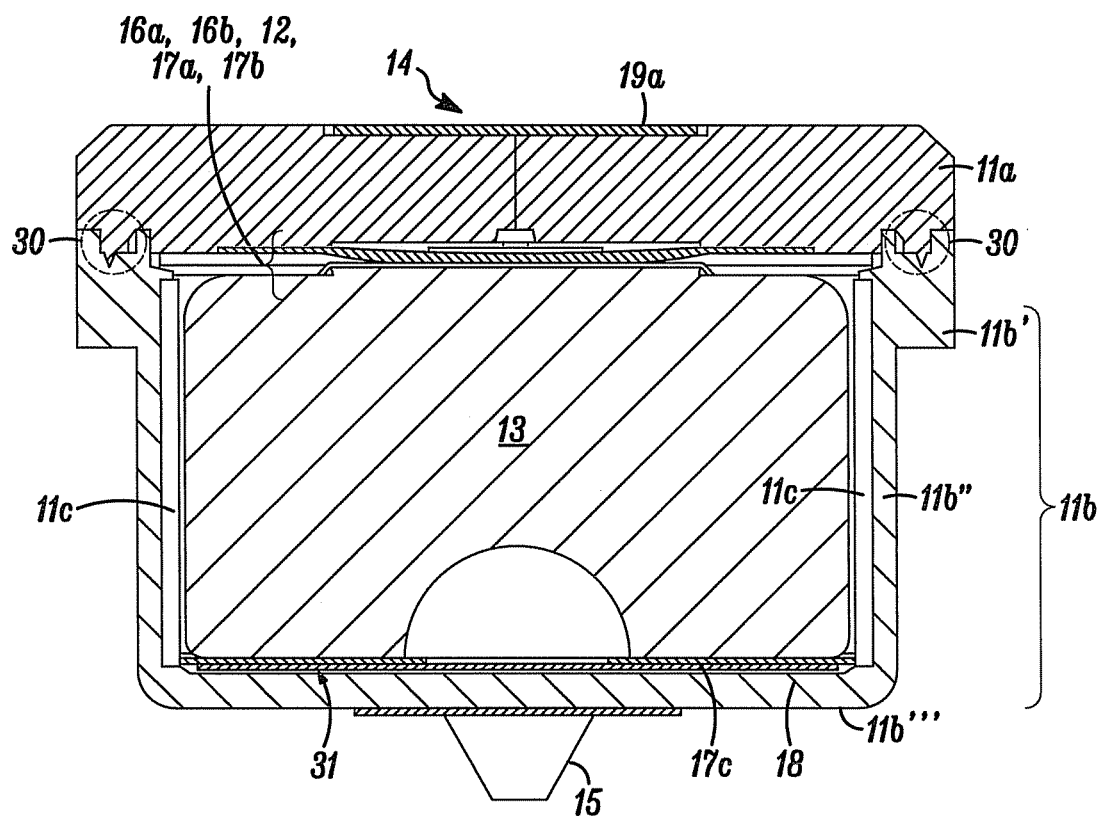
FIG. 3 is a cut-away view of the sensor of FIG. 1.

FIGS. 1, 2 and 3 show an embodiment of an electrochemical gas sensor 10 in accordance with one example embodiment. In the example given, the sensor is an oxygen sensor, but the concepts could equally be applied to other sensor types, including toxic sensors. An example relating to a toxic sensor is discussed below in conjunction with FIG. 4.

The oxygen sensor 10 comprises a plastics housing 11 formed with lid 11a and body 11b, which when assembled, are joined to one another (e.g. by ultrasonic welding) and contain the electrode assembly therewithin. Lid 11a includes an aperture 14 therethrough for gas ingress, typically comprising a capillary and/or diffusion barrier membrane in order to limit the amount of gas entering the sensor. The electrode assembly essentially comprises a gas sensing electrode 12 and a counter electrode 13, each of which is electrically connected in use to a sensing circuit, for example via conductive connection pins 20 and contact clips 21.

FIG. 2a-c shows three examples of suitable sensing circuits in which the sensor 10 could operate. FIG. 2a shows a basic schematic circuit in which the sensing electrode S (as sensing electrode 12) and counter electrode C (anode 13) are connected with a load resistor R between them. The electrolyte E provides ionic communication between the two electrodes while gas access to the sensing electrode is controlled by diffusion barrier D. In use, the current passing through load resistor R is monitored to determine the concentration of target gas reacting at the sensing electrode. In practice, a two-electrode potentiostatic circuit such as that shown in FIG. 2b may be used. The three-electrode circuit shown in FIG. 2c is more often used with certain toxic gas sensors which employ separate reference and counter electrodes.

In use, the gas sensing electrode 12 and counter electrode 13 are each in contact with a liquid electrolyte, typically aqueous potassium acetate or another ionically conducting aqueous electrolyte. The electrolyte is contained within a cavity defined by housing body 11b, which also holds the counter electrode 13. Separator layers 17a, 17b and 17c, which are electrolyte-permeable, may be provided above and below the counter electrode 13 in order to supply electrolyte to the gas sensing electrode 12 while preventing direct contact between the gas sensing and counter electrodes. The separators 17 may be made of glass fiber, for example.

The separator layer 17 divides the interior of the housing 11 into first and second parts or chambers. The first part contains, inter alia, the gas sensing electrode 12 and is bounded by the lid 11a and separator layer 17a. The second part contains, inter alia, the counter electrode 13 and is bounded by the separator layer 17a and housing body 11b.

The gas sensing electrode 12 typically comprises a catalyst such as platinum or carbon, supported on a PTFE membrane. Conductive leads (not shown) are provided to electrically connect the catalytic area to the connection pins 20. The counter electrode 13 here takes the form of a consumable anode which will be oxidized as the cell reaction progresses. Typically, the anode 13 comprises a volume of porous material, such as lead wool, having a large surface area so as to avoid early passivation of the material.

In other sensor types, such as toxic gas sensors, the counter electrode may comprise a catalyst mounted on a PTFE backing tape, in the same manner as the gas sensing electrode 12.

The sensor 10 may also include a number of optional components, such as: a bulk flow disc 16b, adhered to the inside of lid 11a by an adhesive disk 16a. The bulk flow disk may be provided in order to restrict bulk flow of gas into the sensor and in particular reduce pressure transients and temperature-induced pressure transients; a vent 15 and vent membrane 18. A vent 15 may be provided in the form of an aperture through the body of the cavity in order to assist in the avoidance of pressure differentials by enabling the passage of gas into and out of the sensor 10. To prevent escape of liquid through the vent, a gas porous but electrolyte impermeable (e.g. PTFE) membrane 18 may be provided. This is typically heat-sealed to the interior of the body 11b. To avoid gas access through the vent becoming obstructed should the anode expand during operation (e.g. due to oxidation), the counter electrode 13 may be spaced from the vent by providing the electrode 13 with a recess 13a; and outboard of the sensor housing 11, a dust membrane 19a and vent protection membrane 19b may be provided to protect the aperture 14 and vent 15 from dust and moisture.

The geometry of the housing body 11b will depend on the sensor design. In this example, a single large internal cavity is defined, for containing the counter electrode 13, immersed in electrolyte. In other sensor types, the geometry of the housing body 11b may be more complex, to provide for an electrolyte reservoir separate from the electrode stack, with wicking components for transport of electrolyte between the two.

In the present example, the cavity is defined by side walls 11b" (FIG. 3), which are substantially cylindrical, and flat circular walls at either end, the upper wall being provided by housing lid 11a, and the base wall 11b''' being provided by the housing body 11b. Housing body 11b also comprises a flange 11b' encircling the side walls 11b" at their upper edge, which provides a joining surface for welding to the lid 11a.

As shown most clearly in FIG. 3, at least a portion of the walls 11b", 11b''' of the housing body 11b defining the cavity have a base (first layer) and a coating. The main body 11b is formed of a material suited to the forming and joining processes required for manufacturing the housing 11, such as ABS or Noryl™. The lid 11a is typically formed of the same material. Such materials have been found to be well adapted for joining by ultrasonic welding, and also laser drilling. This main body 11b provides a "first layer" of the cavity walls 11b", 11b'''. A "second layer" or coating of material 11c is provided over at least some of the internal surface of the cavity walls 11b", 11b'''. The material making up layer 11c is selected to have a lower water vapor transport rate than that of the main body 11b of the housing (i.e. the "first layer").

Figure 4:
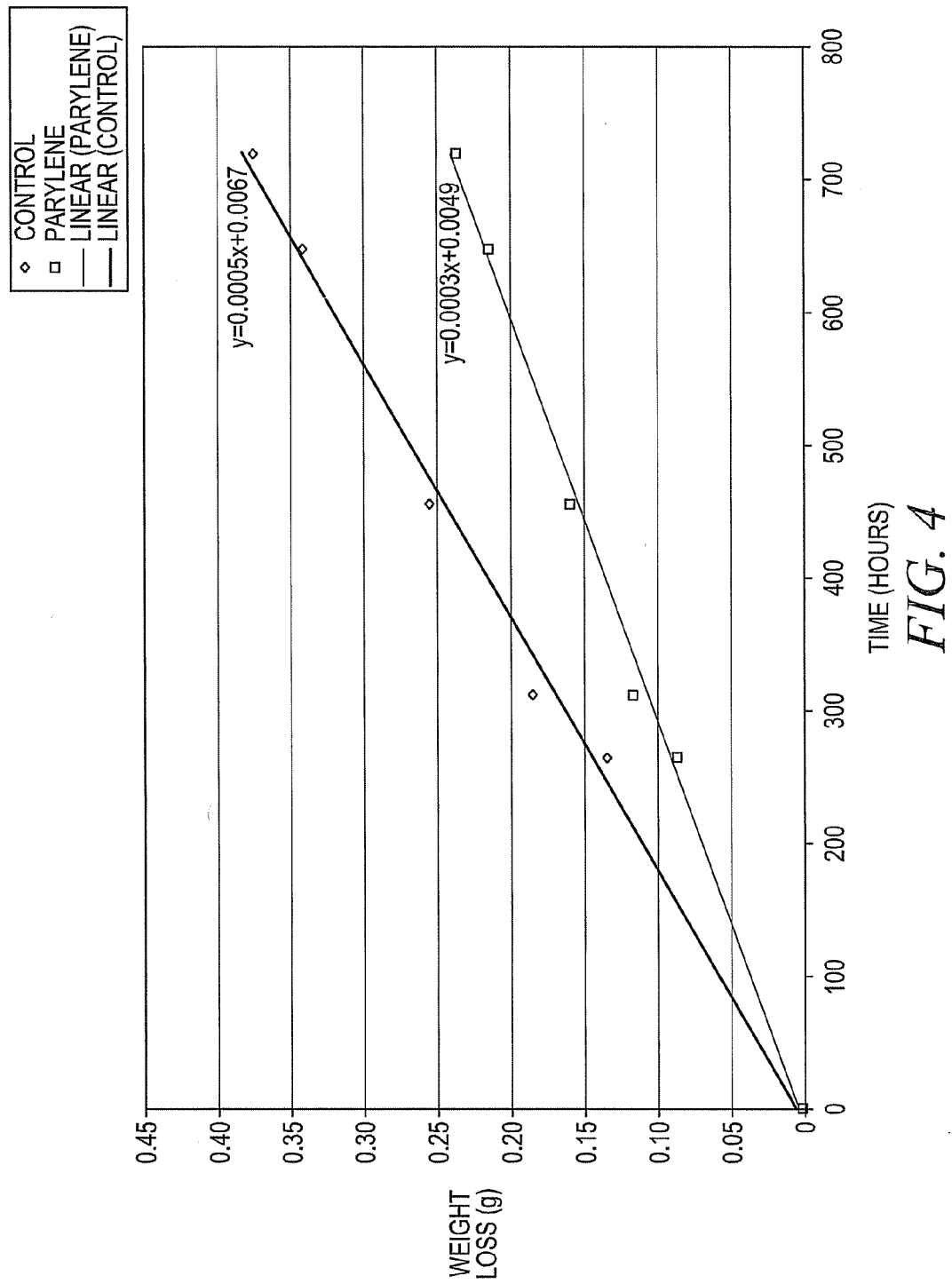
FIG. 4 shows tests results that compares the body of the sensor of FIG. 1 with the bodies of a control group of sensors.

FIG. 4 shows the average effect produced on a group of sensors, including a first control group and a second parylene group. In this case, the first and second groups were identical except that the second group received a 10 μm thick coating (inside and out) of parylene. As can be seen from FIG. 4, the water loss from the parylene group was 35 to 37% less than the control group throughout the 720 hour test period.

The advantage of providing a second layer of low water vapor transport rate is that existing sensor manufacturing processes (ultrasonic welding, laser drilling, etc) will be compatible with the basic housing 11 (e.g. an ABS molding), while the 'skin' layer 11c provides the resistance to water vapor transfer that is required.

In the example shown, the second layer 11c covers the whole interior of the side walls 11b" of the cavity, the base wall 11b'" and the exterior. In other embodiments, a smaller proportion of the cavity wall surface may be covered by the layer 11c: for example, only selected portions of the side walls 11b" and/or base wall 11c'" need carry the second layer.

The second layer 11c may be arranged so as not to cover regions 30 and 31 of the housing body 11b, which are to be subjected to manufacturing processes including ultrasonic welding (at region 30, to join the body 11b to the lid 11a) and laser drilling (at region 31, to produce the vent 15). By doing so, conventional processes can be implemented without the need for modification to take into account the dissimilar material of the second layer 11c. However, this may not be essential, depending on the particular materials selected and the processing techniques in place.

In the embodiment shown, the layer 11c may be provided on the interior surface of the cavity, "inboard" of the housing 11, and this may generally be preferred since the layer 11c (which as noted above may be very thin) is protected from external damage. However, with such a small increase in wall thickness, increasing the external geometry without significantly impacting the instrument becomes possible. As such, in other embodiments, the layer 11c could be provided on the exterior surface of the body 11b ("outboard") to equal effect. Again, the layer 11c could be arranged to cover any portion of the external cavity walls as desired. Whether inboard or outboard, the layer 11c need not be the outermost layer of the wall, as shown in the present embodiment, but could itself be covered by another layer.

The housing body 11b is typically made by injection molding a plastic, such as ABS and as such it is convenient to form the layer 11c in a later CVS process. If any processing regions 30, 31 are to be left uncovered, the CVS process may be designed so as to omit coverage of the second layer 11c in these regions, for example by masking selected areas. Alternatively, the second layer 11c could be applied over the processing regions 30, 31, and then removed by etching or mechanical means.

The electrode assembly can then be stacked within the housing body, which is sealed to housing lid 11a using an appropriate joining technique. The cavity is filled with electrolyte either prior to the application of lid 11a or after, if an entry port is provided (and subsequently sealed).

It should be noted that, while the above description focuses on the depletion of aqueous electrolytes due to water vapor transport, the same principle can be readily applied to the retention of other electrolyte types which are based on non-aqueous solvents, such as acetonitrile or dimethylformamide, which are both well known non-aqueous electrolytes with organic vapours. All that is required is that the material of the second layer 11c is selected as providing a low vapour transport rate for the solvent in question. In practice, the vapour transport mechanism through the cavity walls will depend on both the electrolyte and the wall material in use and so the interaction between these substances will need to be considered in order to select a suitable material for the second layer.

A feature of the described concepts includes an electrochemical gas sensor for the detection of a target gas in an atmosphere. The sensor includes a housing, an aperture in the housing that allows ingress of the target gas, a cathode in a first part of the housing adjacent the aperture, the cathode directly interacts with the target gas that ingresses through the aperture, an anode in a second part of the housing opposite the first part, an electrolyte in the second part of the housing, the electrolyte ionically coupling the cathode and anode and a conformal coating of less than 50 μm directly applied to a surface of an exterior wall of the second part of the housing, the conformal coating retards moisture loss through the exterior wall of the housing.

Although a few embodiments have been described in detail above, other modifications are possible. For example, the logic flows depicted in the figures do not require the particular order shown, or sequential order, to achieve desirable results. Other steps may be provided, or steps may be eliminated, from the described flows, and other components may be added to, or removed from, the described systems. Other embodiments may be within the scope of the following claims.

The invention claimed is:

1. Apparatus comprising:
    an electrochemical gas sensor that detects of a target gas in an atmosphere, the electrochemical gas sensor further comprising:
    a housing;
    an aperture in the housing that allows ingress of the target gas;
    a cathode in a first part of the housing adjacent the aperture, the cathode directly interacts with the target gas that ingresses through the aperture;
    an anode in a second part of the housing opposite the first part;
    an electrolyte in the second part of the housing, the electrolyte ionically coupling the cathode and anode; and
    a conformal coating directly applied to a surface of an exterior wall of the second part of the housing, the conformal coating retards moisture loss through the exterior wall of the housing wherein the conformal coating comprises parylene C.

2. The apparatus as in claim 1 wherein the conformal coating comprises a thickness of less than 50 μm.

3. The apparatus as in claim 1 wherein the electrochemical gas sensor comprises an oxygen sensor.

4. The apparatus as in claim 1 wherein the conformal coating is disposed inside the cavity.

5. The apparatus as in claim 1 wherein the conformal coating comprises a plurality of layers.

6. The apparatus as in claim 1 wherein the housing further comprises acrylonitrile butadiene styrene (ABS).

7. A sensor comprising:
    a housing;
    an aperture in the housing that allows ingress of the target gas;
    a cathode in a first part of the housing adjacent the aperture, the cathode directly interacts with the target gas that ingresses through the aperture;
    an anode in a second part of the housing opposite the first part and an electrolyte in the second part of the housing, the second part defined, in part, by an exterior wall, the electrolyte ionically coupling the cathode and anode; and
    a conformal coating having a thickness of less than 50 μm directly applied to a surface of the exterior wall of the second part of the housing, the conformal coating retards moisture loss through the exterior wall of the housing wherein the coating comprises parylene C.

8. The sensor as in claim 7 wherein the conformal coating comprises a thickness of less than 10 μm.

9. The apparatus as in claim 7 wherein one of the conformal coating is disposed inside the cavity.

10. The apparatus as in claim 7 wherein the housing further comprises acrylonitrile butadiene styrene (ABS).

11. The apparatus as in claim 7 wherein the housing further comprises a polyphenylene oxide (PPO)/polystyrene (PS) blend.

12. A sensor comprising:
a gas sensing electrode and a counter electrode disposed within a housing, and respective conductors that connect the gas sensing electrode and the counter electrode to an external sensing circuit, the housing includes walls defining a cavity containing electrolyte in fluid communication with the gas sensing electrode and counter electrode and wherein the walls further comprise one or more coatings or second layers superimposed on the walls, the one or more coatings or second layers having a lower water vapor transport rate than that of the walls, such that, in use, water vapor transport between the electrolyte and atmosphere through the walls of the housing is reduced wherein the one or more coatings or second layers comprise parylene C.

13. The apparatus as in claim 12 wherein the one or more coatings or second layers further comprise a conformal coating.

14. The apparatus as in claim 12 wherein at least one of the one or more coatings or second layers is disposed inside the cavity.

15. The apparatus as in claim 12 wherein at least one of the one or more coatings or second layers is disposed on an outer surface of the housing.

16. The apparatus as in claim 12 wherein the housing further comprises acrylonitrile butadiene styrene (ABS) or a polyphenylene oxide (PPO)/polystyrene (PS) blend.

* * * * *